United States Patent [19]
Lee

[11] Patent Number: 4,588,530
[45] Date of Patent: May 13, 1986

[54] ANTI-INFLAMMATORY PREDNISOLONE STEROIDS

[75] Inventor: Henry J. Lee, Tallahassee, Fla.

[73] Assignee: Florida Agricultural and Mechanical University, Tallahassee, Fla.

[21] Appl. No.: 502,449

[22] Filed: Jun. 9, 1983

Related U.S. Application Data

[63] Continuation-in-part of Ser. No. 403,710, Jul. 30, 1982, abandoned.

[51] Int. Cl.$^4$ .................................................. C07J 7/00
[52] U.S. Cl. .............................. 260/397.45; 260/397.1
[58] Field of Search ........................... 260/397.1, 397.45

[56] References Cited

U.S. PATENT DOCUMENTS 3,944,577  3/1976  Laurent et al. ................ 260/397.1

FOREIGN PATENT DOCUMENTS 1173467  7/1984  Fed. Rep. of Germany ... 260/397.1

OTHER PUBLICATIONS

Lee et al., "Science" Feb. 1982 (vol. 215) pp. 989–911.
Solimon, M. R. I. et al. "New Anti-Inflammatory Steroids; Steroid-21-Oate Esters, 6th Ann. Clinical Symp. Prog. Res. Clin. Applic. Corticoids, Proceedings of Dec. 1981.
Herman et al. "Steroids" vol. 38 (1981), No. 4, p. 2799.
Lee et al., "Recent Communications in Chemical Pathology and Pharmacology, vol. 27, No. 3, Mar. 1980, pp. 611–614.

*Primary Examiner*—Elbert L. Roberts
*Attorney, Agent, or Firm*—Arthur G. Yeager

[57] ABSTRACT

Derivatives of prednisolone of the formula

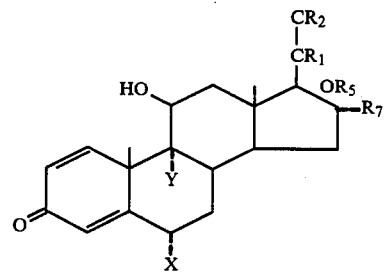

wherein
$CR_1$ is C=O, α-HCOH, β-HCOH, or a mixture of α-HCOH and β-HCOH $CR_2$ is HC(OH) $OR_6$ or HCO when $CR_1$ is C=O;
$CR_2$ is $COOR_3$ or $CONHR_4$ when $CR_1$ is α-HCOH, β-HCOH, or a mixture of α-HCOH and β-HCOH:
$R_3$ is alkyl of 1-5 carbon atoms;
$R_4$ is alkyl of 1-5 carbon atoms, benzyl, or phenethyl;
$R_5$ is hydrogen, acetyl, or benzoyl;
$R_6$ is alkyl of 1-5 carbon atoms;
$R_7$ is α- or β-position of hydrogen, hydroxyl, methyl, acetate esters of 1-5 carbon atoms, or alkoxy of 1-5 carbon atoms; and
X and Y are hydrogen, halogen or methyl;

and process for preparing these compounds. The compounds are useful as anti-inflammatory agents which have reduced side effects.

10 Claims, 1 Drawing Figure

ANTI-INFLAMMATORY PREDNISOLONE STEROIDS

The Government has rights in this invention pursuant to Grants Nos. RO1-AM-21627 and SO6-RR-08111.

This is a continuation-in-part of patent application Ser. No. 403,710 filed July 30, 1982 now abandoned.

BACKGROUND OF THE INVENTION

Although the beneficial effects of natural and semisynthetic corticosteroids in the treatment of inflammatory and allergic conditions have been appreciated for over 30 years, complications arising from steroid therapy have imposed limitations on the clinical use of this class of drugs. The shortcomings are largely inherent in the nature of corticosteroids themselves; not only do glucocorticosteroids possess multiple biological activities, but the structural requirements for various activities appear to be overlapping and inseparable. If the actions of corticosteroids could be localized many of the complications could be eliminated. Although methods for the local administration of steroids have been devised complications associated with local steroid treatment for psoriatic, rheumatologic, eczematous, asthmatic, and ophthalmic patients have been reported. This situation calls for new approaches in developing anti-inflammatory steroids that are devoid of toxicities.

In developing this invention several considerations were kept in mind: (i) corticosteroid pharmacotherapy appears to offer an abundance of agents, but no truly safe drug: (ii) systemic effects of steroids are unnecessary complications which accompany treatment of many inflammatory conditions; (iii) an intact ketol side chain is not an absolute requirement for the anti-inflammatory activity of corticosteroids and (iv) steroid acid esters with intact ring structures corresponding to the known potent glucocorticoids retain anti-inflammatory activity but upon entry into the circulatory system from the site of administration are hydrolyzed to steroid acids that are inactive and readily excreted.

Now it has been found that ester derivatives of steroid-20α-ol-21-oic acid, steroid-20β-ol-21-oic acid, and certain proportionate mixtures thereof applied locally, possess anti-inflammatory activity but do not suppress adrenal function or liver glycogen content in rats.

BRIEF DESCRIPTION OF THE INVENTION

This invention relates to derivatives of prednisolone of the formula.

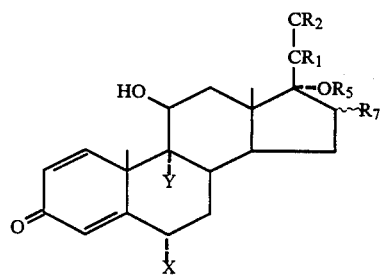

wherein $CR_1$ is C=O, α-HCOH, β-HCOH, or a mixture of α-HCOH and β-HCOH;

$CR_2$ is HC(OH)$OR_6$ or HCO when $CR_1$ is C=O;

$CR_2$ is $COOR_3$ or $CONHR_4$ when $CR_1$ is α-HCOH, β-HCOH, or a mixture of α-HCOH and β-HCOH $R_3$ is alkyl of 1–5 carbon atoms;

$R_4$ is alkyl of 1–5 carbon atoms, benzyl or phenethyl;

$R_5$ is hydrogen, acetyl, or benzoyl;

$R_6$ is alkyl of 1–5 carbon atoms;

$R_7$ is α- or β-position of hydrogen, hydroxyl, methyl, acetate esters of 1–5 carbon atoms, or alkoxy of 1–5 carbon atoms; and X and Y are hydrogen, halogen, or methyl.

The invention also includes a process for preparation and separation of these compounds in which prednisolone in methanol is reacted with oxygen in the presence of copper acetate to prepare 21-dehydroprednisolone (A) and 21-dehydroprednisolone hemiacetal (B) of the formulas:

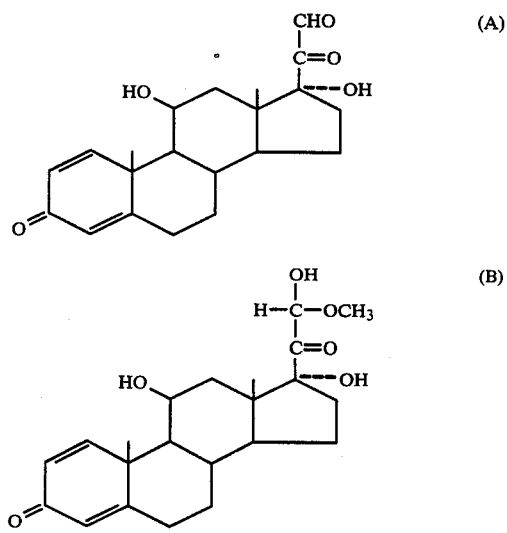

Reacting the dehydroprednisolone with sodium hydroxide to produce 20α- or 20β-dihydroprednisolonic acid of the formulas:

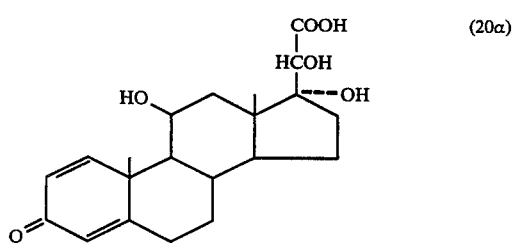

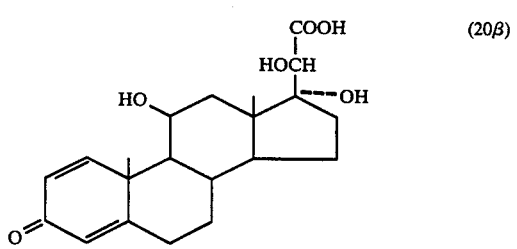

and thereafter reacting the appropriate acid with diazomethane at room temperature to produce the corresponding methyl ester; and the preparation of methyl 20-dihydroprednisolonate directly from prednisolone by the coppa acetate method followed by separation of the α and β epimers by high pressure liquid chromatography.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
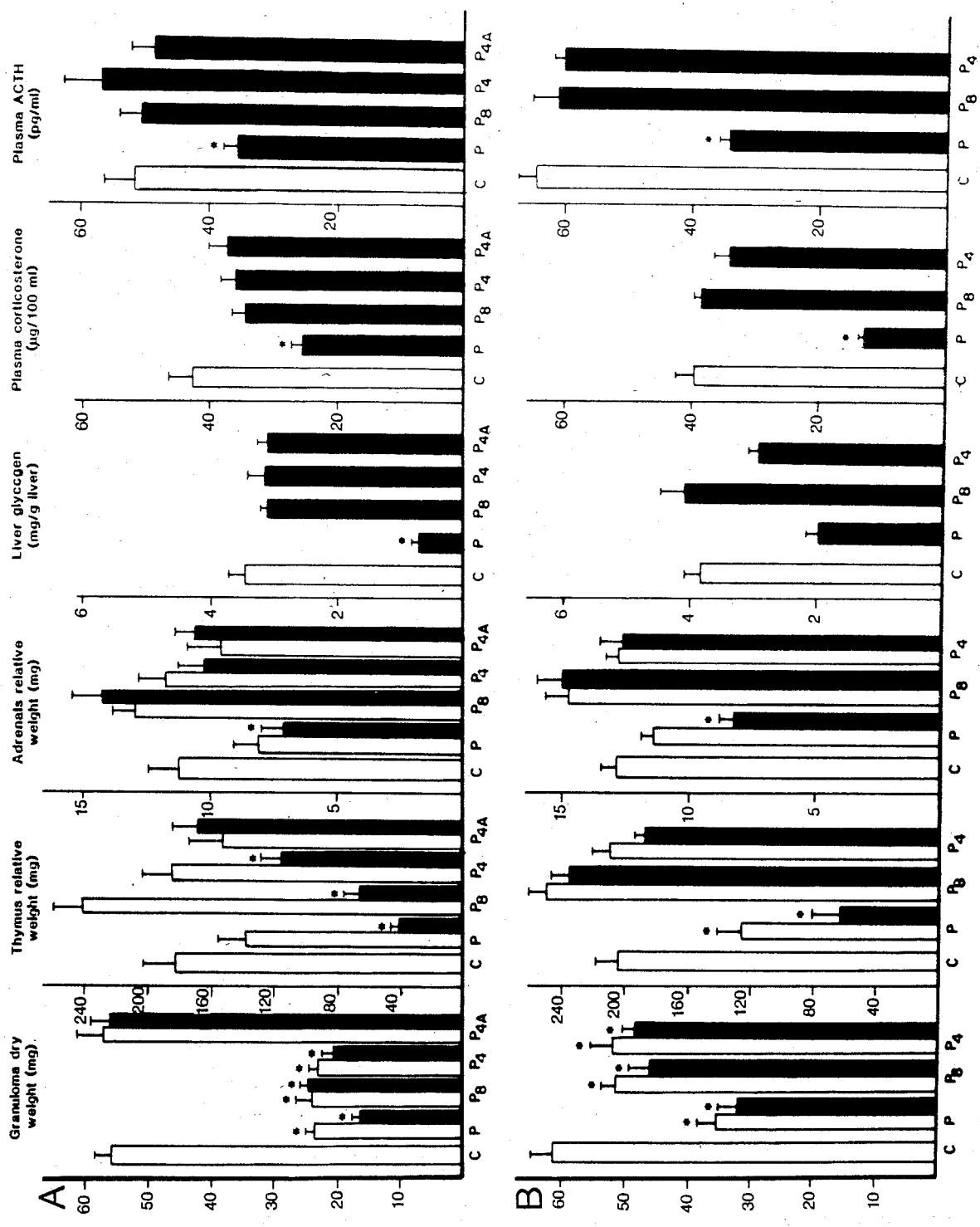
FIG. 1 is a graphical representation of a comparison of the side effects of two derivatives of this invention and unmodified prednisolone as anti-inflammatory agents.

This invention includes a few derivatives of prednisolone of the formula

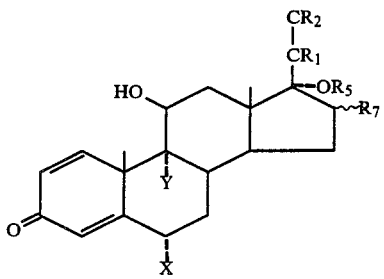

wherein
$CR_1$ is C=O, α-HCOH, β-HCOH, or a mixture of α-HCOH and β-HCOH;
$CR_2$ is $HC(OH)OR_6$ or HCO when $CR_1$ is C=O;
$CR_2$ is $COOR_3$ or $CONHR_4$ when $CR_1$ is α-HCOH, β-HCOH, or a mixture of α-HCOH and β-HCOH;
$R_3$ is alkyl of 1-5 carbon atoms;
$R_4$ is alkyl of 1-5 carbon atoms, benzyl, or phenethyl;
$R_5$ is hydrogen, acetyl, or benzoyl; and
$R_6$ is alkyl of 1-5 carbon atoms;
$R_7$ is α- or β-position of hydrogen, hydroxy, methyl, acetate esters of 1-5 carbon atoms, or alkoxy of 1-5 carbon atoms; and X and Y are hydrogen, halogen, or methyl.

Among the most important of these compounds are those in which $CR_1$ is carbonyl (C=O) and $CR_2$ is a methyl ester group or a hemiacetal group. Another type of important compounds of this invention are those wherein $CR_1$ is α- or β-dihydrocarbonyl (HCOH) and $CR_2$ is a methyl ester or an alkyl carboxamide group. These compounds have been found to have remarkable anti-inflammatory activity and to have substantially reduced side effects which have caused the anti-inflammatory agents of the prior art to be less than fully desirable.

Among the side effects exhibited by the currently used anti-inflammatory agents, such as prednisolone and cortisol, are:
1. adrenal suppression, i.e. the suppression of the production of vital steroids by the adrenal gland which may result in atrophy of the gland with fatal results;
2. weakening of bone structure;
3. wasting of muscular tissue;
4. induction of peptic ulcers;
5. production of hypokalemia, i.e. a reduction of calcium in the body;
6. suppression of mental and/or physical growth in children;
7. thinning of skin; and
8. suppression of the immunization system of the body, which relates directly to the reduction in weight of the thymus gland.

The anti-inflammatory activities of the prednisolone derivaties of this invention were evaluated by cotton pellet granuloma bioassay in rats. Thymolytic, liver glycogen depository, and pituitary adrenal (PA) suppressive effects were monitored. When the rats were under mild anesthesia they were implanted with two cotton pellets (35±1 mg each) subcutaneously, one in each axilla. The local effects of the steroids on granuloma formation were determined by injection of the compound into the cotton pellet before implantation: the systemic effects were evaluated by giving daily intramuscular injections of the compounds after pellet implantation. Seven days after implantation the rats were killed and granuloma, adrenal, thymus, and body weights were measured. Blood samples were analyzed for adrenocorticotrophin (ACTH) and corticosterone, and livers were analyzed for glycogen content.

The actual structure of methyl 20-dihydroprednisolonate is an epimeric mixture of the α- and β-forms of the hydroxyl on the $C_{20}$ atom. The proportions of α- to β-structures may vary within the range of 2-1α:1-2β.

When the term "methyl 20-dihydroprednisolonate" is used herein, it will refer to the epimeric mixture of both α- and β-forms. When either of the α- or β-forms is intended, the approximate designation will be used, e.g. methyl 20α-dihydroprednisolonate or methyl 20β-dihydroprednisolonate.

Prednisolone caused a significant decrease in all the values measured in control rats. In contrast, the new steroids, methyl prednisolonate, methyl 20α-dihydroprednisolonate, methyl 20β-dihydroprednisolonate, and the epimeric mixtures in certain proportions, when they were administered locally, selectively suppressed the weights of granulomas and thymus glands but did not alter adrenal weights, plasma ACTH, plasma corticosterone, or liver glycogen. In this study high doses of steroids were administered deliberately in order to detect any possible systemic toxicities. At the dose level of 2.5 mg per pellet, methyl prednisolonate and methyl 20-dihydroprednisolonate decreased granuloma formation by 56.9 percent and 58.6 percent, respectively. These values are comparable to the 58.3 percent granuloma inhibition obtained with the same dose of the parent compound prednisolone, and suggest that some degree of freedom is available for modifying the ketol side chain of corticosteroids without losing anti-inflammatory activity. With doses of 5 mg. per pellet, prednisolone exhibited a higher inhibitory effect on granuloma formation (70.29 percent) than either methyl prednisolonate (55.6 percent) or methyl 20-dihydroprednisolonate (36.3 percent). It was found that upon separation of methyl 20-dihydroprednisolonate into its α- and β-components, the β-component was 2.3 times more active than the mixture. A metabolite of the esters, which showed an anti-inflammatory activity was devoid of thymolytic, glycogen depletion, and adrenal suppressive effects.

Although the steroid acid esters retained effective anti-inflammatory activity when administered intramuscularly for 7 days, their activity was weaker than that of prednisolone. At doses of 2.5 mg/kg. methyl prednisolonate and methyl 20-dihydroprednisolonate decreased granuloma formation by 16.07 and 15.2 percent, respectively, whereas prednisolone suppression was 42.6 percent. A similar trend in the relative potency of the steroids was observed at doses of 5 mg./kg. In contrast to the parent compound, methyl prednisolonate and methyl 20-dihydroprednisolonate exhibited no thymolytic or PA suppressive activities.

At doses of 5 mg/kg. methyl prednisolonate did not deplete liver glycogen at all, whereas methyl 20-dihydroprednisolonate slightly decreased liver glycogen content. At a dose of 10 mg/kg administered intramuscularly for 7 days, methyl 20-dihydroprednisolonate suppressed granuloma formation to the same degree as prednisolone administered at 2.5 mg/kg for the same period. However, the equipotent dose of methyl 20-dihydroprednisolonate did not suppress plasma ACTH or plasma corticosterone, although the parent compound did decrease their concentration.

In FIG. 1 there may be seen graphically the comparison of the effects of prednisolone (P), methyl prednisolonate (P8), methyl 20-dihydroprednisolonate (P4), 20-dihydroprednisolonic acid (P4A) as compared to a control (C) with no anti-inflammatory agent present. The graph shows local treatment (A) and systemic treatment by intramuscular injection (B). Unshaded bars represent a dosage of 2.5 mg. and black shaded bars a dosage of 5.0 mg. per cotton pellet in (A) and per kg of body weight in (B). The T-shaped symbol at the top of each bar represents the maximum value and the top of each bar represents the minimum value of the six animals tested for each measurement. An asterisk (*) indicates a significantly different value from the control.

Test results are shown in Tables 1-2. The following procedures were employed. Adult male Sprague-Dawley rats weighing 120-140 g were maintained on standard laboratory chow with water ad libitum and kept under controlled condition for one week prior to their use. Cotton pellets weighing 35±1 mg cut from dental rolls were impregnated with steroid solution in acetone (0.2 or 0.4 ml) and the solvent was removed by evaporation. The cotton pellets were subsequently injected with 0.2 ml aqueous solution of antibiotics (1 mg penicillin G and 1.3 mg dihydrostreptomycin/ml). Two cotton pellets were implanted s.c., one in each axilla of the rat under light ether anesthesia. Cotton pellets containing only the antibiotic solution were similarly implanted in the control rats. Seven days later, the animals were sacrificed and the two pellets, with their adhering granulomas, were removed, dried for 48 h in an oven at 60° C. and weighed. The increment in dry weight (difference between the initial and final pellets weight) is taken as a measure of granuloma formation. The adrenal, thymus and final body weight were also recorded. The adrenal and thymus weights were expressed as relative weights (mg tissue/100 g body weight).

For local and systemic effects of steroids, one cotton pellet impregnated with tested steroid was implanted in one axilla of the rat and the other cotton pellet containing only the antibiotic was implanted in the other axilla.

For measuring plasma corticosterone level, blood samples were collected th rough cardiac puncture in heparinized tubes which were immediately centrifuged for 10 min. The plasma was removed and stored at −20° C. Plasma corticosterone levela were assayed by the flourometric method. In some instances there is reported the use of α-P4 and/or β-P4 because it has been found that P4 exists as an epimeric mixture of the two epimers. P2 is 21-methoxy prednisolone. P4 is methyl 20-dihydroprednisolonate. P8 is methyl prednisolonate. P21 is n-propyl 20-dihydroprednisolonamide. Plasma corticosterone is related directly to adrenals weight since the former is produced by the adrenal gland. In order to exhibit reduced side effects the thymus weight, adrenals weight and plasma corticosterone should be maintained as closely as possible to the values shown by the control. Granuloma inhibition percentage should be as high as possible to provide good anti-inflammatory activity.

TABLE 1

| Steroid Used | Dosage mg/cotton pellet | % Granuloma Inhibition | Relative Thymus Weight mg/100 mg granuloma | Plasma Corticosterone mg/100 ml plasma |
|---|---|---|---|---|
| None (control) | — | — | 285.27 ± 5.04 | 27.48 ± 6.58 |
| $P_2$ | 2.5 | 64.55 | 170.15 ± 7.74 | 27.23 ± 5.19 |
| $P_{21}$ | 2.5 | — | 237.28 ± 9.89 | 7.02 ± 1.05 |
| None (control) | — | — | 276.81 ± 19.45 | 35.49 ± 4.23 |
| Prednisolone | 2.5 | 68.33 | 93.58 ± 5.59 | 26.9 ± 6.25 |
| $P_4$ | 2.5 | 41.59 | 246.19 ± 21.53 | 30.19 ± 3.29 |
| $P_4$ | 2.5 | 22.17 | 243.52 ± 28.64 | — |
| None (control) | — | — | 255.15 ± 15.11 | 52.28 ± 9.73 |
| Cortisol | 2.5 | 68.92 | 140.62 ± 10.06 | 33.57 ± 17.46 |
| Prednisolone | 2.5 | 73.03 | 83.75 ± 11.31 | 36.88 ± 3.90 |
| $P_4$ (NaOH process) | 2.5 | 16.34 | 241.13 ± 12.23 | 44.16 ± 3.89 |
| $P_4$ (Cu(Ac)$_2$ process) | 2.5 | 66.76 | 193.06 ± 17.32 | 48.7 ± 5.54 |
| Mixture of α-$P_4$ and β-$P_4$ (7:1) CuAc$_2$ process | 2.5 | 14.19 | 258.25 ± 17.26 | 42.63 ± 4.97 |
| None (control) | — | — | 294.74 ± 17.03 | 56.03 ± 9.67 |
| Predisolone | 2.5 | 70.93 | 88.10 ± 11.16 | 35.3 ± 6.87 |
| Mixture of α-$P_4$ and β-$P_4$ (1:1) | 2.5 | 35.20 | 1215.24 ± 16.29 | 56.44 ± 7.19 |
| Mixture of α-$P_4$ and β-$P_4$ (9:1) | 2.5 | 37.76 | 216.32 ± 16.89 | 49.56 ± 9.02 |

($P_4$ prepared by sodium hydroxide method)

TABLE 2

| Steroid Used | Dosage mg/cotton pellet | % Granuloma Inhibition | Relative Thymus Weight mg/100 mg granuloma | Relative Adrenal Weight mg/100 mg granuloma |
|---|---|---|---|---|
| None (control) | — | — | 218.53 ± 18.70 | 12.80 ± 0.78 |
| Prednisolone | 2.5 | 74.76 | 108.38 ± 10.14 | 11.89 ± 0.38 |
| $P_4$ | 2.5 | 65.28 | 224.05 ± 5.19 | 14.15 ± 0.96 |

($P_4$ prepared by copper acetate method)

Derivatives of this invention wherein $R_3$ is ethyl, propyl, butyl, t-butyl, and pentyl all show slightly less activity in reducing granuloma than when $R_3$ is methyl, and the reduction in side effects is comparable for all forms of $R_3$. The derivative wherein $CR_2$ is $CONHR_4$ is particularly useful for the treatment of hyperadrenalism since this derivative suppresses adrenal function. $R_4$ is preferably n-propyl, although other lower alkyl groups of 1–5 carbon atoms produce similar results.

This new class of steroids inhibits the release of marker enzymes from rat liver lysosomes in vivo and vitro and replaces [$^3$H] dexamethasone from receptor prepared from rat liver cytosol in the presente of 2 mM $Na_2MoO_4$. 20-Dihydroprednisolonic acid failed to stabilize lysosomal membranes or replace labeled desamethasone bound to the receptor.

These data substantiate the hypothesis that both steroid keto acid and hydroxy acid esters which retain the intact ring structures of potent corticosteroids possess anti-inflammatory activity but upon entry into the circulatory system from the administration site are hydrolyzed to inactive steroid acids. Thus, these acid ester derivatives have minimal adverse systemic effects. The fact that anti-inflammatory activity of the steroid acid esters was not accompanied by PA suppression after local and systemic administration suggests that the anti-inflammatory activity of corticosteroids may be separate from the PA suppressive activity.

Typically, the C-20 carbonyl function has been considered essential for anti-inflammatory activity. No glucocorticoid currently in clinical use has a reduced keto group; that is, a hydroxy group, at the C-20 position as is present in methyl 20-dihydroprednisolonate. It is therefore significant that the corresponding C-20 hydroxy compound is not only an active local anti-inflammatory agent but also is a potent as the C-20 keto compound.

The prednisolone derivatives of this invention are made from prednisolone as a starting material. If prednisolone is reacted with methanol and oxygen in the presence of copper acetate for about one hour the product is dehydroprednisolone which may be treated with sodium hydroxide to produce 20-dihydroprednisolonic acid, which, in turn may be reacted with diazomethane to produce methyl 20-dihydroprednisolonate. If prednisolone is reacted with methanol and oxygen in the presence of copper acetate for a long period of time, e.g. a week, the product is methyl 20-dihydroprednisolonate. The more detailed description of these and other syntheses are given below.

Melting points were determined on Thomas Capillary melting point apparatus and are uncorrected. U. V. Spectra were measured for solution in methanol with a Beckman spectrophotometer UV 5260. IR Spectra were obtained with a Perkin-Elmer spectrophotometer. $^1$H-NMR spectra were determined at 270 MHz on a Bruker HX-270 and the chemical shifts are reported in ppm downfield from an internal tetramethylsilane. Mass spectra were recorded on a Finnigan 4510 GCMS using 70 eV source. Analytical data for the elements were within +0.4% of the theoretical values. HPLC consisted of a 250×10 mm ID stainless steel column packed by Zorbax and the chromatography pump was set at flow rate 4 ml/min. and the wavelength detector (Waters Associations Model 450) was set at 254 nm.

I SYNTHESIS OF METHYL 20-DIHYDROPREDNISOLONATE (P4)

(Methyl 11β, 17α,20-trihydroxy-3-oxo-1,4-pregnadiene-21-oate)

Method Using Copper Acetate For 1.5 hours

To a solution of prednisolone (3.6 g, 10 mmol) in methanol (250 ml) was added a solution of copper acetate (1 g,15 mmol) in methanol (250 ml). The mixture was set aside for 10 min. and then air was bubbled ror 1.5 h at room temperature. After addition of 1% $NaHCO_3$ solution containing ethylenedinitrilotetraacetic acid disodium salt(EDTA) (0.15 g), the methanol was evaporated under vacuo at 40° C. The steroid was extracted with ethyl acetate and the extracts were washed with 1% $NaHCO_3$ and $H_2O$. The ethyl acetate solution was dried with anhydrous $Na_2SO_4$ and the solvent was evaporated to dryness under vacuo at 40° C. The residue was dissolved in acetone and filtered. The filtrate contained mainly dehydroprednisolone and the precipitate was 21-dehydroprednisolone hemiacetal. The filtrate was evaporated to dryness and the residue was crystallized from acetone—phosphate buffer (pH 7.4) to give 21-dehydroprednisolone as a white needle crystals. Yield 51.3%, m.p. 115°–16° C. $R_f$ 0.62 (acetone-ethyl acetate, 1:2). I.R. 3440, 3940 (OH), 1720 (20 and 21-C=O), 1665, 1610 and 890 cm$^{-1}$ ($\Delta^4$-3-C=O). $^1$H-NMR (Me$_2$SO,d$_6$) 0.85 (s, 3H, 13-CH$_3$), 1.39 (s, 3H, 10-CH$_3$), 4.28 (m, 1H, 11α-H), 5.93 (s, 1H, 4-H), 6.15 (dd, J=10 and 2 Hz, 1H, 2-H) and 7-36 (d, J=10 Hz, 1H, 1-H). Mass spectra m/e (%) M+ at 358 (1.39), 340 (1.6), 322 (1.1), 283 (2.78), 147 (25.26), 122 (100), 121 (78,95), 107 (15.63), 91 (33.30(, Anal. ($C_{21}H_{26}O_2.H_2O$) C,H.

The precipitate 21-dehydroprednisolone hemicetal was crystallized from dioxane-hexane mixture, yield 25.6%, m.p. 189°–90° C., $^1$H-NMR (CDCl$_3$) 0.95 (s, 3H, 13-CH$_3$), 1.48 (s, 3H, 10-CH$_3$), 3.48 (s, 3H, 21-OCH$_3$), 4.40 (m, 1H, 11α-H), 5.96 (s, 1H, 4-H), 6.2 (dd, J=10 and 2 Hz, 1H, 2-H and 7.38 (d, J=10 Hz, 1H, 1-H). The mass spectra showed the parent peak at 358 (M+-MeOH). Anal. ($C_{22}H_{30}O_6$) C, H.

11β, 17α, 20-trihydroxy-3-oxo-1,4-pregnadiene-21-oic acid

To a solution of 21-dehydroprednisolone (2 g, 5 mmol) in acetone (5 ml) or a suspension of 21-dehydroprednisolone hemiacetal (2 g, 5 mmol) in acetone (5 ml) with stirring under nitrogen, an ice-cold mixture of $H_2O$ (80 ml) and 2N NaOH (2.5 ml) was added. The reaction mixture was continuously stirred at 0° C. for 4 h. The unreacted starting material was extracted with ethyl acetate and the aqueous phase was acidified with 1N HCl. The resulted solution was extracted with ethyl acetate. The combined ethyl acetate extracts was washed with $H_2O$ and dried with anhydrous $Na_2SO_4$. The solvent was evaporated and the residue was crystallized from acetone-petroleum ether (40°–60° C.) to give white needle crystals of 20-dihydroprednisolonic acid yield 70%, m.p. 210°–13° C.

One gram of 20-dihydroprednisolinic acid was quantitatively converted to its methyl ester, methyl 20-dihydroprednisolonate, using ethereal solution of diazomethane. The ester was crystallized from acetone-hexane mixture. $R_f$ 0.6 (acetone-ethyl acetate, 1:2). The ratio of 20-α epimer to 20-β epimer determined by HPLC was 11:1. IR 3460, 2940 (OH), 1735, 1270, 1240CM-1(COOCH$_3$). Anal. ($C_{22}H_{30}O_6$) C, H.

Method Using Copper Acetate For 1 Week

To a solution of prednisolone (6 g, 17 mmol) in MeOH (500 ml) was added a solution of copper acetate (1.5 g, 7.5 mmol) in MeOH (500 ml). The mixture was bubbled with air for one week after 10 min. standing. The reaction was stopped by adding 1% NaHCO$_3$ solution (400 ml) containing EDTA (3 g). MeOH in the reaction mixture was removed by evaporation under vacuo at 40°. The remaining aqueous phase was extracted with ethyl acetate. The extracts were washed with 2% NaHCO$_3$ solution, H$_2$O, and dried with anhydrous Na$_2$SO$_4$. The solvent was evaporated under vacuo at 40° C. to give a crude mixture of the 20α- and 20β-epimers of methyl 20-dihydroprednisolonate (4.6 g) which contains a minor quantity of 21-dehydroprednisolone. To remove 21-dehydroprednisolone, the crude ester was dissolved in MeOH (80 ml) and added into a solution of NaHSO$_3$ (1 g) in H$_2$O (200 ml). After being heated on a steam bath for 15 min and cooled to room temperature, the ester was extracted with ethyl acetate. The extract was washed with water and dried with anhydrous Na$_2$SO$_4$. The solvent was evaporated under vacuo at 40° C. and the residue was chromatographed on 28×850 mm silica gel column using hexane:CH$_2$Cl$_2$:acetone, 50:20:30 (500 ml) then hexane:CH$_2$Cl$_2$:acetone, 40:20:40 (1 L) as eluent, collecting 12 ml per 10 min. Crystallization of the material obtained from the fractions 70-150 from acetone-hexane mixture afforded a pure mixture of the 20-α and 20-β epimers of methyl 20-dihydroprednisolonate; yield 55%; HPLC analysis showed that the ratio of the α-epimer to the β-epimer to be 1:1.3; Rf 0.6 (acetone-ethyl acetate, 1:2); IR 3450, 2940 (OH), 1735, 1240, 1170 cm$^{-1}$ (COOCH$_3$). Anal. (C$_{22}$H$_{30}$O$_6$) C, H.

Separation of the Epimeric Mixture into α- and β-Epimers

The epimeric mixture of methyl 20-dihydroprednisolonate (850 mg) was dissolved in MeOH (5 ml) with heat. When the solution was left to cool, the 20α-epimer crystallized out. The filtrate was kept for separation of recovery of the 20β-epimer: Recrystallization from MeOH afforded pure 20α-epimer (400 mg) as plate-like crystals, m.p. 254°-55° C. λmax$^{243}$ $^{nm,}$ ε16,000. $^1$H-NMR (Me$_2$SO, d$_6$): 1.13 (s, 3H, 13-CH$_3$), 1.35 (s, 3H, 10-CH$_3$), 3.79 (s,3H, 21-OCH$_3$), 4.19 (s,1H, 20-H), 4.43 (d, J=3 Hz, 1H, 11α-H), 6.03 (s, 1H, 4-H), 6.27 (dd, J=10 and 2H2, 1H, 2-H) and 7.24 (d, J=10 Hz, 1H, 1-H). Mass spectra m/e (%) M+ at 390 (1.38), 372 (1.44), 354 (0.34), 285 23.25), 265 (26.45), 147 (39.84), 122 (95.2), 121 (100), 107 (20.1), 91(37.87).

HPLC analysis of the above filtrate showed that the ratio of 20α-epimer to 20β-epimer to be 1:7. The filtrate, diluted with 50% aqueous MeOH to 15 ml, was injected into HPLC (500 ml each injection) and the fractions corresponding to the 20β-epimer were collected. MeOH was evaporated under vacuo and the 20β-epimer was extracted with ethyl-acetate. After washing the extract with H$_2$O then drying with anhydrous Na$_2$SO$_4$, the solvent was removed by evaporation under vacuo to dryness. The residue was crystallized from acetone-hexane mixture to give pure 20β-epimer (350 mg) as prismatic crystals. m.p. 171°-3° C. Rf 0.59 (acetone-ethyl acetate, 1:2). λmax$^{244}$ $^{nm,}$ ε17,400. $^1$H-NMR (CdCl$_3$), 1.15 (s, 3H, 13-CH$_3$), 1.45 (s, 3H, 10-CH$_3$), 3.81 (s, 3H, 21-OCH$_3$), 4.36 (s, 1H, 20-H), 4.43 (m, 1H, 11α-H), 6.01(s, 1H, 4-H), 6.28 (dd, J=10 and 2 Hz, 1H, 2-H) and 7.28 (d, J=10 Hz, 1H, 1-H). Mass spectra showed M+ at 390 and having the same fragmentation pattern as the 20α-epimer.

II SYNTHESIS OF METHYL PREDNISOLONATE (P8)

(Methyl 11β, 17α-dihydroxy-3,20-dioxo-1,4-pregnadiene-21-oate:)

To a solution of 1.4 g of 21-dehydroprednisolone in a mixture of 45 ml methylene choloride and 25 ml methanol was added 400 mg potassium cyanide and 3 ml of glacial acetic acid. The reaction mixture was stirred for 15 minutes at room temperature, then diluted with methylene chloride, and washed with water. The organic layer was dried over anhydrous sodium sulphate and then evaporated. The residue was chromatographed on silica gel using acetone-hexane 1:2 as eluent. Recrystallization from acetone-hexane gave 200 mg of methyl 11β17α-dihydroxy-3,20-dioxo-1,4-pregnadiene-21-oate as white crystals m.p. 225°-227° C.

III SYNTHESIS OF N-PROPYL 20-DIHYDROPREDNISOLONATAMIDE (P21)

n-propyl 11β, 17α20-trihydroxy-3-oxo-1,4-pregnadiene-20-carboxamide)

To a solution od 370 mg (1 mmol) of 20-dihydroprednisolonic acid was added a solution of 227 mg of dicyclohexylcarbodiimide (DCC) and 203 mg of N-hydroxybenzotriazole in 25 ml of methylene chloride. The reaction mixture was stirred at 4° C. over night. The precipitated dicyclohexylurea (DCU) was removed by filtration and 84 μl (1 mmol) of n-propylamine was added to the filtrate and stirring with cooling at 4° C. was continued for 24 hours. The solution was then extracted with 1%, sodium bicarbonate solution, 1N hydrochloric acid, washed with water and then dried over anhydrous sodium sulphate. The solvent was evaporated and the residue was purified by column chromatography using silica gel employing chloroform:methanol 9:1 as eluent.

| m.p. 251-253° C. Analysis calcd. for C$_{24}$H$_{35}$NO$_5$ | | | | |
|---|---|---|---|---|
| | C | H | N | O |
| found | 69.04 | 8.45 | 3.35 | 19.18 |
| | 68.70 | 8.20 | 3.21 | |

The steroid methyl 20-dihydroprednisolonate is as mentioned above an epimeric mixture of the α- and β-epimers of the hydroxyl group on the carbon atom in the 20-position. These two isomers have been separated and tested separately and as mixtures to determine relative activity of these epimeric forms and mixtures thereof. The mixtures were prepared by either the copper acetate method or the sodium hydroxide method described elsewhere herein, The α- and β-epimers were separated by fractional crystallization from methanol and by preparative HPLC(high pressure liquid chromatography).

The 20β-epimer exhibited 2.3 times higher activity than that of the 20α-epimer. The reconstituted mixture of the two epimers to a ratio of 1:1 showed a 56.3% local anti-inflammatory activity. In addition neither epimer nor the epimeric mixture suppressed adrenal and thymus weights nor decreased plasma corticosterone at dose level of 2.5 mg/pellet. A linear dose response of 20β-epimer on the inhibition of granuloma formation at doses of 0.5, 1.0, 2.0 and 2.5 mg/cotton pellet shows a direct correlation of decreasing granuloma weight with increasing dosages (28.5 mg. at 0.5 mg. dose to 17.5 mg at 2.5 mg dose). These results show that the orientation of the hydroxyl group at C-20 of the steroidal glycolate plays an important role in local anti-inflammatory activity, and that the local anti-inflammatory activity of the epimeric mixture is mainly due to the β-epimer. The results are shown in Table 3.

TABLE 3

| Steroid Used | Dosage mg/cotton pellet | % Granuloma Inhibition | Plasma Corticosterone mg/100 ml |
|---|---|---|---|
| Control | 0 | — | 25.76 ± 4.06 |
| Prednisolone | 2.5 | 65.65 | 16.23 ± 6.87 |
| Epimeric Mixture[a] | 2.5 | 22.17 | 21.19 ± 3.29 |
| Epimeric Mixture[b] | 2.5 | 60.96 | 28.05 ± 5.48 |
| α-epimer | 2.5 | 26.51 | 25.43 ± 4.12 |
| β-epimer | 2.5 | 62.14 | 23.47 ± 8.07 |
| Epimeric Mixture[c] | 2.5 | 56.53 | 25.95 ± 7.19 |

[a]Prepared by NaoH process, ratio of epimers was 11α:1β
[b]Prepared by Cu(Ac)2 process, ratio of epimers was 1α:1.3
[c]Reconstituted mixture of α- and β-epimers in a ratio of 1:1

A comparison of local and systemic activity of the steroids was made by implanting one cotton pellet treated with steroid in one axilla and the other cotton pellet untreated in the other axilla of the rats. The results as seen in Table 4 show that the epimeric mixture of isomers and the 20-β epimer do not inhibit granuloma formation of untreated cotton pellet, unlike parent compound, prednisolone which inhibits granuloma formation of both cotton pellets.

TABLE 4

| Steroid Used | Treated (T) Untreated (U) | Dosage mg/cotton pellet | % Granuloma Inhibition | Plasma Corticosterone mg/100 ml |
|---|---|---|---|---|
| Control | | 0 | — | 25.76 ± 4.06 |
| Prednisolone | (T) | 2.5 | 64.66 | 17.53 ± 5.78 |
| | (U) | | 22.76 | |
| Epimeric mixture | (T) | 2.5 | 62.08 | 27.23 ± 4.56 |
| | (U) | | 0.0 | |
| β-epimer | (T) | 2.5 | 54.54 | 23.75 ± 4.35 |
| | (U) | | 0.0 | |

The preparation of the epimeric mixture of methyl 20-dihydroprednisolonate is described above in either of two procedures. The separation of the mixture into the two epimers was accomplished as described above.

Another series of tests were run on the amide derivatives of 20-dihydroprednisolonic acid and on a 17-benzoate derivative of prednisolone. The amide derivatives all have the basic structure

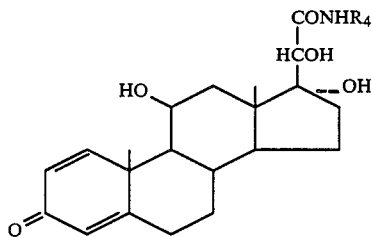

where R4 is —CH2CH2CH3; —CH2C6H5; or —CH2CH2C6H5; and wherein the C-20 structure may be α-HCOH or β-HOCH. These compounds are synthesized by preparing 20-dihydroprednisolonic acid as described above and treating the acid with the appropriate amine as follows:

A solution of 0.74 g (2 mmol) of the acid 454 mg of DCC and 403 mg of N-hydroxybenzotriazole in a mixture of methylene chloride (25 ml) and tertrahydrofuran (5 ml), was stirred overnight at 4° C. The dicyclohexylurea precipitate was removed by filtration and 2 mmol of the proper amine was added to the filtrate. After 24 hours at 4° C., the solution was washed with 0.1M sodium bicarbonate solution, 1N HCl, and twice with water. The dried organic layer was then evaporated and the residue was further purified by column chromatography on silica gel using chloroform-methanol (9:1) as eluent.

The 17-benzoate derivative has the formula:

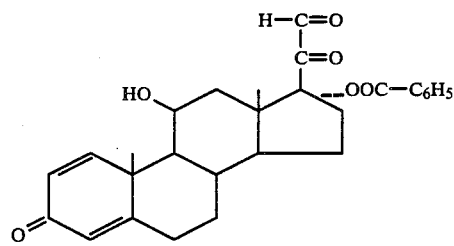

and was prepared from prednisolone as follows:

A solution of 4 g. (11 mmols) of prednisolone in 200 ml. of dioxane and 320 ml. of benzene, was treated with 1 g. of pyridinium p-toluenesulfonate and 10 ml. of trimethylorthobenzoate and the mixture was heated under reflux for 24 hours. The reaction mixture was concentrated under reduced pressure and then diluted with ethyl acetate. The organic layer was washed with water, dried over anhydrous sodium sulfate and then evaporated under reduced pressure to an oil. A mixture of 80 ml. of glacial acetic acid and 2 ml. of water was added to the oily residue and set aside for one hour at room temperature. The mixture was then diluted with water, extracted with ethyl acetate. The extract was washed with 2% sodium bicarbonate solution, then with water, dried over anhydrous sodium sulfate, and the solvent was evaporated under reduced pressure. The precipitate was filtered and washed with acetone to afford 2.75 g. (60%) of white crystals of 17α-benzoyloxy-11β, 21-dihydroxy-3,20-dioxo-1,4-pregnadiene. m.p. 256°-258° C. A solution of 1.5 g. (3.3 mmols) of this compound in 125 ml. of methanol was mixed with a solution of 0.38 g. (2 mmols) of cupric acetate in 125 m. of methanol and the mixture was set aside for five minutes. The air was then bubbled for 30 minutes. After that, 100 ml. solution of 1% sodium bicarbonate containing 1 g. ethylenedinitrilotetraacetic acid disodium salt(EDTA) was added and then the solvent was evaporated under reduced pressure at 40° C. The aqueous residue was extracted with ethyl acetate and the combined extract was washed with 2% sodium bicarbonate solution and then with water. The organic phase was dried over anhydrous sodium sulfate and then the solvent was evaporated under reduced pressure qt 40° C. The residue was crystallized from acetone-hexane mixture to give 1.28 g. (80%) of 17α-benzoyloxy-11β, 21-dihydroxy-21-methoxy-3,20-dioxo-1,4-pregnadiene. m.p. 121°-123° C.

These compounds were tested on rats to determine anti-inflammatory activity as described above with the results shown in Table 5.

TABLE 5

| Steroid Used | Dosage mg/cotton pellet | % Granuloma Inhibition | Plasma Corticosterone mg/100 ml. |
|---|---|---|---|
| Control | — | — | 35.49 ± 4.23 |
| 20β,21-N—propyl amide | 2.5 | — | 7.02 ± 1.05 |
| 20α,21-N—propylamide | 2.5 | 62.18 | 40.14 ± 4.90 |
| 20α and 20β-mixture, 21 phenethyl amide | 2.5 | — | 10.67 ± 1.72 |
| 20α- and 20β-mixture 21 benzyl amide | 2.5 | 22.86 | — |
| 17 benzoate-21-aldehyde | 2.5 | 66.04 | 34.93 ± 3.04 |

The derivities of this invention have been illustrated as applied to the basic steroid structure of prednisolone, but it is to be understood that these derivatives are equally applicable to any steroid structure of the pregnan-21-oic acid series of the formula

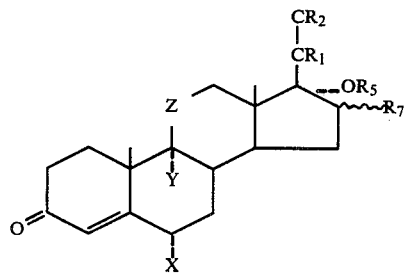

Wherein $CR_1$, $CR_2$, $R_5$, and $R_7$ have the same meanings as given above; X is hydrogen, halogen, or methyl; Y is hydrogen, halogen, or methyl; Z is methylene, carbonyl, β-hydroxymethylene, β-acyloxymethylene, or when Y is halogen, β-halomethylene.

While the invention has been described with respect to certain specific embodiments it will be appreciated that many modifications and changes may be made by those skilled in the art without departing from the spirit of the invention. It is intended, therefor, by the appended claims to cover all such modifications and changes as fall within the true spirit and scope of the invention.

What is claimed as new and what is desired to secure by Letters Patent of the United States is:

1. Derivatives of prednisolone of the formula

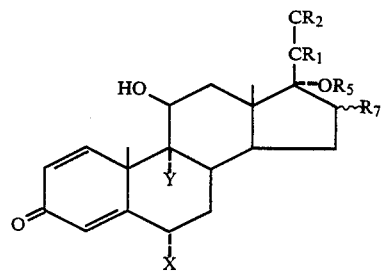

wherein
$CR_1$ is C=O, α-HCOH; β-HCOH, or a mixture of α-HCOH and β-HCOH;
$CR_2$ is HC(OH)OR$_6$ when $CR_1$ is C=O;
$CR_2$ is CONHR$_4$ when $CR_1$ is α-HCOH, β-HCOH, or a mixture of α-HCOH and β-HCOH;
$R_3$ is alkyl of 1-5 carbon atoms;
$R_4$ is alkyl of 1-5 carbon atoms, benzyl, or phenethyl;
$R_6$ is alkyl of 1-5 carbon atoms;
$R_7$ is α- or β-position of hydrogen, hydroxyl, methyl, acetate ester of 1-5 carbon atoms, or alkoxy of 1-5 carbon atoms; and
X and Y are hydrogen, halogen, or methyl.

2. The derivatives of claim 1 wherein $CR_1$ is α-HCOH, β-HCOH, or a mixture of α-HCOH and β-HCOH and $CR_2$ is CONHR$_4$.

3. The derivative of claim 1 wherein $CR_1$ is an epimeric mixture of α- and β-epimers of HCOH.

4. The derivative of claim 2 wherein $R_4$ is a n-propyl.

5. The derivative of claim 1 wherein $CR_1$ is C=O and $CR_2$ is HC (OH)OCH$_3$.

6. The method of preparing methyl 20-dihydroprednisolonate of the formula

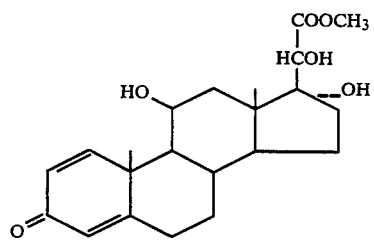

which comprises reacting prednisolone in methanol with oxygen in the presence of copper diacetate for about one hour to prepare dehydroprednisolone of the formula

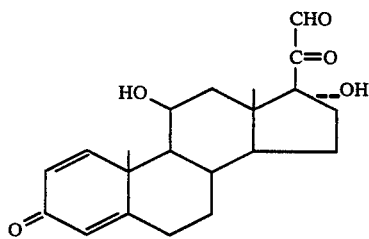

reacting dehydroprednisolone with sodium hydroxide in an atmosphere of nitrogen of about 0° C. to produce 20-dihydroprednisolonic acid of the formula

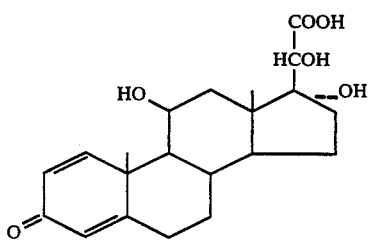

and reacting said 20-dihydroprednisolonic acid with diazomethane at room temperature to produce methyl 20-dihydroprednisolonate of the formula 7. The method of preparing methyl prednisolonate of the formula

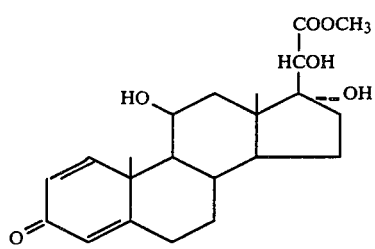

which comprises reacting prednisolone in methanol with oxygen in the presence of copper diacetate for about one hour to prepare dehydroprednisolone of the formula

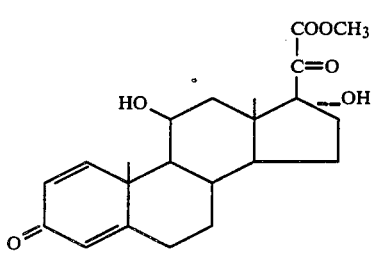

reacting said dehydroprednisolone in acetone with 0.1 molar phosphate ion at pH of 6.8 with methylene blue to produce prednisolonic acid of the formula

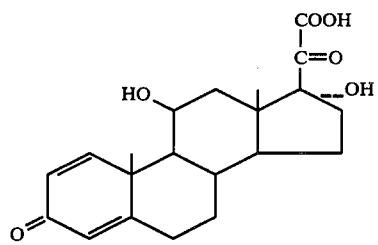

and reacting said prednisolonic acid with diazomethane at room temperature to produce methyl prednisolonate of the formula

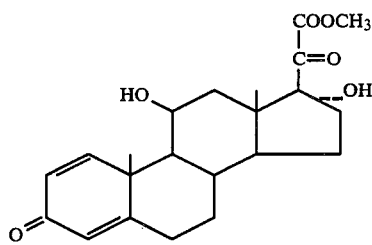

8. The method of preparing n-propyl-20-dihydroprednisolonamide which comprises reacting 20-dihydroprednisolonic acid with dicyclohexylcarbodiimide and N-hydroxybenzotriazole and reacting the product thereof with n-propylamine.

9. The method of preparing 21-methoxy prednisolone which comprises reacting prednisolone with methanol and oxygen in the presence of copper acetate for about one hour and crystallizing from the methanol 21-methoxyprednisolone.

10. The method of separating the 20-α-hydroxy and the 20-β-hydroxy components from a mixture of those components in methyl 11β, 17α, 20-trihydroxy-3-oxo-1,4-pregnadiene-21-oate which comprises dissolving said mixture in methanol and allowing the solution to separate into a filtrate and a precipitate of the 20-α-hydroxy component, diluting the filtrate with aqueous methanol and subjecting the diluted filtrate to high pressure liquid chromatography, collecting and accumulating the fractions therefrom, evaporating the methanol from the accumulated fractions, washing and drying the product of evaporation, and recovering a pure 20-β-hydroxy component.

* * * * *